United States Patent [19]

Clemènce et al.

[11] 4,078,076
[45] Mar. 7, 1978

[54] NOVEL P-(4-TETRAHYDROPYRANYL)-PHENOXY-COMPOUNDS

[75] Inventors: François Clemènce, Rosny-sous-Bois; Daniel Humbert; Robert Fournex, both of Paris, all of France

[73] Assignee: Roussel UCLAF, Paris, France

[21] Appl. No.: 690,010

[22] Filed: May 26, 1976

[30] Foreign Application Priority Data

Jun. 3, 1975  France .................. 75 17271

[51] Int. Cl.² ............... A61K 31/35; C07D 309/22
[52] U.S. Cl. ................... 424/283; 260/345.1; 260/345.7 R; 260/345.8 R
[58] Field of Search .......... 260/345.7, 345.8, 345.7 R, 260/345.8 R; 424/283

[56]     References Cited

U.S. PATENT DOCUMENTS 3,755,603   8/1973   Harrison et al. ............... 260/345.7
3,772,332   11/1973  Allais et al. .................... 260/345.7
3,992,386   11/1976  Schacht et al. .................. 260/345.8

Primary Examiner—Nicky Chan
Attorney, Agent, or Firm—Hammond & Littell

[57]        ABSTRACT

Novel pyranic derivatives of the formula

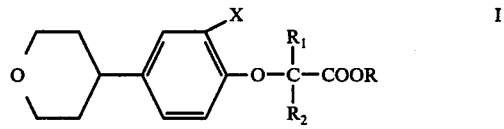

wherein R is selected from the group consisting of hydrogen, alkyl of 1 to 6 carbon atoms and cations of alkali metals, alkaline earth metals, aluminum, amines and ammonium $R_1$ and $R_2$ are individually selected from the group consisting of hydrogen and alkyl of 1 to 4 carbon atoms and X is selected from the group consisting of hydrogen, chlorine and bromine having hypolipemic activity and reducing the level of total lipids in plasma.

16 Claims, No Drawings

NOVEL P-(4-TETRAHYDROPYRANYL)-PHENOXY-COMPOUNDS

STATE OF THE ART

Belgium Pat. No. 804,452 describes as having hypolipemiant activity compounds of the formula

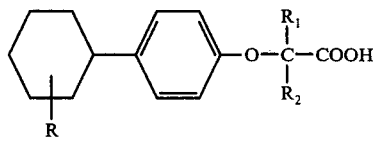

OBJECTS OF THE INVENTION

It is an object of the invention to provide the novel compounds of formula I and novel intermediates therefor as well as a novel process for their production.

It is another object of the invention to provide novel hypolipemic compositions and to provide a novel method of inducing hypolipemic activity in warm-blooded animals including humans.

These and other objects and advantages of the invention will become obvious from the following detailed description.

THE INVENTION

The novel pyran derivatives of the invention have the formula

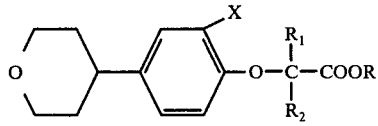

wherein R is selected from the group consisting of hydrogen, alkyl of 1 to 6 carbon atoms and cations of alkali metals, alkaline earth metals, aluminum, amines and ammonium, $R_1$ and $R_2$ are individually selected from the group consisting of hydrogen and alkyl of 1 to 4 carbon atoms and X is selected from the group consisting of hydrogen, chlorine and bromine.

The alkyl group of 1 to 6 carbon atoms may be methyl, ethyl, n-propyl, isopropyl, n-butyl, isobutyl, tert.-butyl, pentyl or hexyl. Examples of amines which may be used to form the amine salts of formula I are monoalkylamines such as methylamine, ethylamine or propylamine; dialkylamines such as dimethylamine, diethylamine or di-n-propylamine; or trialkylamine such as triethylamine.

Among the preferred compounds of formula I are those where X is hydrogen or chlorine, $R_1$ is methyl, $R_2$ is hydrogen or methyl and X is hydrogen or chlorine.

The novel process of the invention for the preparation of compounds of formula I comprises reacting 4-phenyltetrahydropyran with a nitration agent to form 4-(p-nitrophenyl)-tetrahydropyran, reacting the latter with a reducing agent to obtain 4-(p-aminophenyl)-tetrahydropyran, subjecting the latter to reaction with a diazotation agent in an acid media followed by decomposition by the Sandmeyer reaction to obtain 4-(p-hydroxyphenyl)-tetrahydropyran, optionally reacting the latter with a chlorination or bromination reagent to form the corresponding 4-(m-halo-p-hydroxyphenyl)-tetrahydropyran and reacting either of the 4-(m-X-p-hydroxyphenyl) tetrahydropyrans wherein X is hydrogen, chlorine or bromine with a compound of the formula

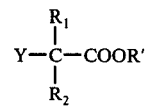

wherein $R_1$ and $R_2$ have the above definition, R' is alkyl of 1 to 6 carbon atoms and Y is chlorine or bromine to obtain the corresponding compound of formula I wherein R is alkyl of 1 to 6 carbon atoms which if desired may be hydrolyzed to form the free acid of formula I wherein R is hydrogen and the latter may be salified or esterified by the usual methods.

In the preferred embodiments of the process of the invention, the nitration is effected with nitric acid in acetic acid anhydride or in the presence of an acid such as acetic acid or sulfuric acid or with sodium nitrate in the presence of an acid such as sulfuric acid. The reduction is effected with a reducing agent in an acid, basic or neutral medium.

The reduction may be effected with zinc in the presence of an alkali metal hydroxide, ferrous sulfate in the presence of ammonium hydroxide, sodium amalgam, aluminum amalgam or ammonium sulfide in an alkaline medium. The reduction may be effected with hydrogen in the presence of a catalyst such as platinum oxide, rhenium oxide, nickel, Raney nickel or palladium or with an alkali metal borohydride in the presence of a catalyst such as palladium or copper in a neutral medium. The reduction in an acid media may be effected with zinc in hydrochloric acid, tin or stannous chloride in hydrochloric acid, aluminum in the presence of sulfuric acid or zinc in the presence of ammonium chloride.

The diazotation agent may be an alkali metal nitrite such as sodium nitrite or potassium nitrite in the presence of an acid such as sulfuric acid.

The chlorination agent may be gaseous chlorine, sulfuryl chloride sodium hypochlorite, phosphorus trichloride or phosphorus oxychloride and the reaction may be effected in the absence or presence of an organic solvent such as carbon tetrachloride, benzene or toluene. The reaction is preferably effected at room temperature although it may range from room temperature to reflux of the solvent. The bromination may be effected under analogous conditions.

The reaction of the 4-(m-X-p-hydroxyphenyl)-tetrahydropyrans with a compound of formula II is preferably effected in the presence of a strong base in an organic solvent. The strong base may be alkali metal alcoholate such as sodium ethylate or potassium ethylate or an alkali metal hydride such as sodium hydride. The organic solvent may be methanol, ethanol, propanol, ether or tetrahydrofuran and the reaction temperature may vary from −10° C to the reflux temperature of the solvent. Also useful are alkali metal carbonates such as potassium carbonate or sodium carbonate in a ketone solvent such as acetone, methyl ethyl ketone, methyl isobutyl ketone or in dimethylformamide.

The compounds of formula I wherein R is alkyl of 1 to 6 carbon atoms may be prepared by esterification of the corresponding free acid with an alkanol of 1 to 6 carbon atoms in an acid medium such as hydrochloric acid or p-toluene sulfonic acid. Also, the corresponding acid chloride may be reacted with a lower alkanol of 1 to 6 carbon atoms.

The salts of formula I may be prepared by reacting the free acid of formula I with the corresponding mineral or organic base such as sodium hydroxide, potassium hydroxide, calcium hydroxide, aluminum hydroxide, sodium ethylate, potassium ethylate, ammonium hydroxide or an amine such as ethylamine, methylamine or triethylamine. The reaction is preferably effected in one or more solvents such as water, ethyl ether, ethanol or acetone.

In a modification of the process of the invention, the compounds of formula I wherein R is hydrogen and $R_1$ and $R_2$ are methyl may be prepared by reacting a 4-(m-X-p-hydroxyphenyl)-tetrahydropyran with acetone and chloroform in the presence of a strong base and then acidifying the product. The strong base may be an alkali metal hydroxide such as potassium hydroxide or sodium hydroxide and the temperature may vary from room temperature to the reflux point of the reaction mixture. The acidification may be effected with an acid such as hydrochloric acid, sulfuric acid or an acid anhydride such as sulfurous acid anhydride.

The novel hypolipemic compositions of the invention are comprised of an effective amount of at least one compound of formula I and an inert pharmaceutical carrier. The compositions may be solids or liquids such as tablets dragees, gelules, granules, suppositories or injectable solutions or suspensions prepared in the usual manner.

The inert pharmaceutical carrier may be those usually used such as talc, arabic gum, lactose, starch, magnesium stearate, cacao butter, aqueous or non-aqueous vehicles, fatty bodies of animal or vegetable origin, paraffinic derivatives, glycols, preservatives or diverse wetting agents, dispersants or emulsifiers.

The compositions of the invention have hypolipemic activity and reduce the level of total lipids in the plasma. They are useful in the treatment of acute or chronic hyperlipemia, of coronary insufficiency, of cardiac insufficiency of atheromateous origin or chronic anginic states.

Among the preferred compositions of the invention are those where X is hydrogen or chlorine, $R_1$ is methyl, $R_2$ is hydrogen or methyl and X is hydrogen or chlorine.

The novel method of the invention for inducing hypolipemia in warm-blooded animals, including humans, comprises administering to warm-blooded animals a hypolipemically effective amount of at least one compound of formula I. The compounds may be administered orally, rectally or parenterally. The usual useful dose is 2 to 50 mg/kg.

The novel intermediates of the invention have the formula

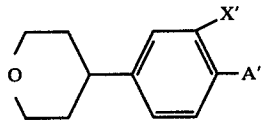

III wherein X' is hydrogen, chlorine or bromine when A is —OH and X' is hydrogen when A' is —NO$_2$ or —NH$_2$.

The compounds of formula II may be prepared by known processes such as described in Bull. Soc. Chim., Vol. 49 (1931), p. 1428, Bull, Soc. Chim., (1947), p. 58 and Chem. Ab., Vol. 53 (1959), p. 16020e and Vol. 55 (1961), p. 4254f and 24,548c.

In the following examples there are described several preferred embodiments to illustrate the invention. However, it should be understood that the invention is not intended to be limited to the specific embodiments.

EXAMPLE 1

2-methyl-2-[p-(4-tetrahydropyranyl)-phenoxy]-propanoic acid

STEP A: 4-(p-nitrophenyl)-tetrahydropyran

A solution of 32.4 g of 4-(phenyl)-tetrahydropyran [Ber., Vol. 56 (1923), p. 2013] in 60 ml of acetic acid was added at −10 to −12° C over an hour to a solution of 120 ml of concentrated nitric acid and 50 ml of acetic acid and the mixture was stirred for 30 minutes at −10° C. 100 ml of ice and 100 ml of water were added to the mixture and the mixture was filtered. The recovered precipitate was washed with water and dried to obtain 35 g of 4-(p-nitrophenyl)-tetrahydropyran melting at 124° C.

STEP B: 4-(p-aminophenyl)-tetrahydropyran 140 g of stannous chloride were added over 30 minutes at room temperature to a suspension of 43.4 g of 4-(p-nitrophenyl)-tetrahydropyran in 435 ml of concentrated hydrochloric acid and the mixture was heated at 60° C for 2 hours and was cooled to 4° C. The mixture was filtered and the recovered crystals were washed with water and dissolved in a mixture of 300 g of iced water and 300 ml of 2N sodium hydroxide. The solution was stirred at room temperature and was then filtered. The recovered crystals were dissolved in methylene chloride and the aqueous alkaline phase was extracted with methylene chloride. The combined methylene chloride phases were washed with water and dried and evaporated to dryness. The residue was crystallized from isopropyl alcohol to obtain 27 g of 4-(p-aminophenyl)-tetrahydropyran melting at 122° C.

STEP C: 4-(p-hydroxyphenyl)-tetrahydropyran

A solution of 5.2 g of sodium nitrite in 10 ml of water was added to a mixture of 13 g of 4-(p-aminophenyl)-tetrahydropyran and 100 ml of concentrated sulfuric acid cooled to 5° C and the mixture was stirred at 5° C for 30 minutes. The mixture was poured into a solution of 100 ml of water and 10 ml of concentrated sulfuric acid heated to 75°–80° C and the mixture was held at 75°–80° C for 15 minutes and was then cooled to 4° C. The mixture was filtered and the recovered crystals were washed with water and dried to obtain 12.7 g of 4-(p-hydroxyphenyl)-tetrahydropyran melting at 164° C.

STEP D: 2-methyl-2-[p-(4-tetrahydropyranyl)-phenoxy]-propanoic acid 13.5 g of 4-(p-hydroxyphenyl)-tetrahydropyran and 15.2 g of sodium hydroxide were added to a solution of 200 ml of acetone and 15 ml of chloroform and the mixture was refluxed for 6 hours. The mixture was returned to room temperature and was filtered. The recovered precipitate was dissolved in 50 ml of water and the solution was washed with ether and acidified with sulfur dioxide. The mixture was extracted with ether and the ether extracts were washed with water, dried and evaporated to dryness to obtain 9.6 g of 2-methyl-2-[p-(4-tetrahydropyranyl)-phenoxy]-propanoic acid melting at 112° C.

Analysis: $C_{15}H_{20}O_4$ Calculated: %C 68.16 %H 7.63
Found: 68.5 7.8

EXAMPLE 2 ethyl 2-methyl-2-[p-(4-tetrahydropyranyl)-phenoxy]-propanoate 2.2 ml of thionyl chloride were added at 15° C to a mixture of 7 g of 2-methyl-2-[p-(4-tetrahydropyranyl)-phenoxy]-propanoic acid, 70 ml of benzene and 3.5 ml of triethylamine and the mixture was stirred for 2 hours at room temperature and was then filtered. The filtrate was slowly added to 250 ml of 5.4N hydrochloric acid in ethanol and the mixture was stirred for 12 hours at room temperature and was then concentrated to dryness. The residue was added to 100 ml of ether and the solution was washed with a saturated sodium bicarbonate solution and then with water. The solution was dried and evaporated to dryness and the oily residue was distilled under reduced pressure to obtain 6.5 g of ethyl 2-methyl-2-[p-(4-tetrahydropyranyl)-phenoxy]-propanoate with a boiling point of 138°–140° C at 0.1 mm Hg.

Analysis: $C_{17}H_{24}O_4$ Calculated: %C 69.83 %H 8.27 Found: 69.7 8.1

EXAMPLE 3

2methyl-2-[o-chloro-p-(4-tetrahydropyranyl)-phenoxy]-propanoic acid

STEP A: 4-(4-hydroxy-3-chlorophenyl)-tetrahydropyran 10 ml of sulfuryl chloride were added with stirring to a mixture of 14.1 g of 4-(p-hydroxyphenyl)-tetrahydropyran and 40 ml of carbon tetrachloride and the mixture was heated to 45°–50° C for 16 hours. The mixture was concentrated to dryness under reduced pressure and the residue was chromatographed over silica gel. Elution with methylene chloride yielded a crystal product which was dissolved in 200 ml of N sodium hydroxide and the solution was washed with ether and acidified with 2N hydrochloric acid. The mixture was extracted with ether and the organic phase was washed with water, then an aqueous sodium bisulfite solution and then with water. The extracts were dried and evaporated to dryness to obtain 6.4 g of 4-(4-hydroxy-3-chlorophenyl)-tetrahydropyran melting at 123°–125° C.

STEP B: 2-methyl-2-[o-chloro-p-(4-tetrahydropyranyl)-phenoxy]-propanoic acid 2.6 ml of chloroform were progressively added to a mixture of 5.4 g of 4-(4-hydroxy-3-chlorophenyl)-tetrahydropyran, 5.2 g of sodium hydroxide and 36 ml of acetone and the mixture was refluxed for 18 hours. The mixture was cooled and concentrated to dryness and the residue was dissolved in 100 ml of water. The solution was washed with ether, acidified with 2N hydrochloric acid and was then extracted with ether. The ether phase was washed with water and was then extracted with a saturated aqueous sodium bicarbonate solution and then with water. The combined aqueous phases were washed with ether and acidified with 2N hydrochloric acid. The aqueous phase was extracted with ether and the ether phase was washed with water, dried and concentrated to dryness to obtain 3.9 g of 2-methyl-2-[o-chloro-p-(4-tetrahydropyranyl)-phenoxy]-propanoic acid melting at 141° C.

Analysis: $C_{15}H_{19}C_4$ Calculated: %C 60.30 %H 6.41 %Cl 11.87 Found: 60.4 6.4 11.9

EXAMPLE 4 ethyl 2-[p-(4-tetrahydropyranyl)-phenoxy]-propanoate

A suspension of 8.9 g of 4-(p-hydroxyphenyl)-tetrahydropyran in 50 ml of ethanol was added to a mixture of 1.15 g of sodium in 100 ml of ethanol and the mixture was stirred for 2 hours at room temperature and was then cooled to 0° C. 7.82 ml of ethyl 2-bromopropanoate were added to the mixture which was then allowed to return to room temperature and the mixture was refluxed for 5 hours. The mixture was evaporated to dryness and the residue was dissolved in a mixture of 100 ml of ether, 45 ml of water and 5 ml of 2N hydrochloric acid. The aqueous phase was removed by decanting and the organic phase was washed with 2N sodium hydroxide, was dried and evaporated to dryness under reduced pressure to obtain 7.9 g of ethyl 2-[p-(4-tetrahydropyranyl)-phenoxy]-propanoate with a boiling point of 138°–140° C at 0.05 mm Hg.

Analysis: $C_{16}H_{22}O_4$ Calculated: %C 69.04 %H 7.97 Found: 69.3 8.1

The same product was also prepared by the same process except the reflux step was effected with acetone in the presence of potassium carbonate.

EXAMPLE 5

2-[p-(4-tetrahydropyranyl)-phenoxy]-propanoic acid 7.6 g of ethyl 2-[p-(4-tetrahydropyranyl)-phenoxy]-propanoate were added to a solution of 17 ml of 2N sodium hydroxide and 100 ml of ethanol and the mixture was stirred for 2 hours at room temperature and then was refluxed for 30 minutes. The mixture was evaporated to dryness and the residue was dissolved in 20 ml of N sodium hydroxide. The solution was washed with ether and acidified with 4N hydrochloric acid. The mixture was filtered and the recovered crystals were washed with water and dried. The product was crystallized from a 50–50 cyclohexane-ethyl acetate mixture to obtain 6.1 g of 2-[p-(4-tetrahydropyranyl)-phenoxy]-propanoic acid melting at 156° C.

Analysis: $C_{14}H_{18}O_4$ Calculated: %C 67.18 %H 7.25 Found: 67.4 7.4

EXAMPLE 6 ethyl 2-[p-(4-tetrahydropyranyl)-phenoxy]-butanoate

A solution of 44.6 g of 4-(p-hydroxyphenyl)-tetrahydropyran in 50 ml of ethanol was added at 20° C to a mixture of 5.75 g of sodium in 250 ml of ethanol and the mixture was stirred for one hour and then was cooled to 0° C. 55.1 ml of ethyl 2-bromo-butyrate were added to the reaction mixture which was then allowed to return to 20° C and was refluxed overnight. The ethanol was evaporated and the residue was taken up in 50 ml of 1N sodium hydroxide and 250 ml of methylene chloride. The aqueous phase was decanted and was extracted again with methylene chloride. The organic phases were dried and evaporated to dryness to obtain 56.3 g of raw product which was rectified under reduced pressure to obtain 40 g of ethyl 2-[p-(4-tetrahydropyranyl)-phenoxy]-butanoate with a boiling point of 143° C. at 0.3 mm Hg.

Analysis: $C_{17}H_{24}O_4$ Calculated: %C 69.83 %H 8.27 Found: 69.6 8.4

EXAMPLE 7

2-[p-(4-tetrahydropyranyl)-phenoxy]-butanoic acid

A mixture of 14.6 g of ethyl 2-[p-(4-tetrahydropyranyl)-phenoxy]-butanoate, 100 ml of ethanol and 40 ml of 2N sodium hydroxide was stirred at 20° C for 24 hours and then refluxed for an hour. The ethanol was evaporated and the residue was taken up in 100 ml of 0.5N sodium hydroxide. The solution was washed with ether and acidified with concentrated hydrochloric acid and was extracted with methylene chloride. The extracts were dried and evaporated to dryness to obtain 13.2 g of raw product which was crystallized from cyclohexane to obtain 12.2 g of 2-[p-(4-tetrahydropyranyl)-phenoxy]-butanoic acid melting at 127° C.

Analysis: $C_{15}H_{20}O_4$ Calculated: %C 68.16 %H 7.63 Found: 68.3 7.6

EXAMPLE 8

Tablets were prepared containing 25 mg of 2-methyl-2-[p-(4-tetrahydropyranyl)-phenoxy]-propanoic acid and sufficient excipient of lactose, starch, talc and magnesium stearate for a tablet weighing 500 mg.

Gelules were prepared containing 25 mg of 2-methyl-2-[p-(4-tetrahydropyranyl)-phenoxy]-propanoic acid and sufficient excipient of talc, magnesium stearate and aerosil for a final gelule weight of 500 mg.

PHARMACOLOGICAL DATA

A. Hypolipemic Activity

This test was effected on groups of 8 male rats of the Sprague-Dawley S.P.F. strain weighing about 200 g and the animals received a diet which contained 50% of saccharose and was enriched with cholesterol (1%). The animals were treated for 10 days with the test product which was administered as a suspension in water containing carboxymethylcellulose with an esophagus probe. The animals were fasted and killed 16 hours after the last administration by carotidiene section and blood samples were taken to determine the level of triglycerides, of cholesterol and total lipids by the following methods.

The triglyceride levels were determined by the semi-automatic technique of Kessler et al [Automation in Analytical Chemistry, New York (1965), p. 341] as modified by Claude et al [Ann. Biol. Clin., Vol. 26 (1968) 3-4, p. 451]. The cholesterol level was determined by the technique of Levine [Symposium Technicon, Vol. 1 (1967), p. 25] adapted to an auto-analyzer system. The nephelemetric level of total lipids was determined by the semi-automatic determination of Girard et al [Symposium Technicon, Paris, 1970]. The percent of variation of the triglycerides, cholesterol and total lipids after administration of different levels of the test product as compared to the control animals is reported in Table I for 2-methyl-2-[p-(4-tetrahydropyranyl)-phenoxy]-propanoic acid.

TABLE I

| | | % Variation | | |
|---|---|---|---|---|
| Product | Dose in mg/kg | Trigly-cerides | Choles-terol | Total lipids |
| 2-methyl-2-[p-(4-tetrahydropyranyl)-phenoxy]-propanoic acid | 20 | −30 | −23 | −26 |
| | 50 | −49 | −26 | −24 |
| | 100 | −60 | −52 | −56 |

B. Acute toxicity

The acute toxicity was determined on groups of 10 mice weighing between 18 and 22 g and the products were administered intraperitoneally in suspension in carboxymethylcellulose. The 50% lethal dose ($DL_{50}$) was determined after one week and the results are in Table II.

TABLE II

| Product of Example | $DL_{50}$ in mg/kg |
|---|---|
| 1 | >1000 |
| 2 | >1000 |

Various modifications of the products and methods of the invention may be made without departing from the spirit or scope thereof and it should be understood that the invention is to be limited only as defined in the appended claims.

We claim:

1. A compound of the formula

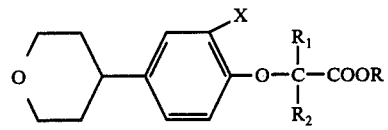

wherein R is selected from the group consisting of hydrogen, alkyl of 1 to 6 carbon aoms and cations of alkali metals, alkaline earth metals, aluminum, alkylamines and ammonium, $R_1$ and $R_2$ are individually selected from the group consisting of hydrogen and alkyl of 1to 4 carbon atoms and X is selected from the group consisting of hydrogen, chlorine and bromine.

2. A compound of claim 1 wherein X is hydrogen or chlorine.

3. A compound of claim 2 wherein $R_1$ is methyl and $R_2$ is hydrogen or methyl.

4. A compound of claim 1 which is 2-methyl-2-[p-(4-tetrahydropyranyl)-phenoxy]-propanoic acid.

5. A compound of claim 1 which is ethyl 2-methyl-2-[p-(4-tetrahydropyranyl)-phenoxy]-propanoate.

6. A compound of claim 1 which is 2-methyl-2-[o-chloro-p-(4-tetrahydropyranyl)-phenoxy]-propanoic acid.

7. A compound of claim 1 which is ethyl 2-[p-(4-tetrahydropyranyl)-phenoxy]-propanoate.

8. A compound of claim 1 which is 2-[p-(4-tetrahydropyranyl)-phenoxy]-propanoic acid.

9. A compound of claim 1 which is 2-[p-(4-tetrahydropyranyl)-phenoxy]-butanoic acid.

10. A compound of claim 1 which is ethyl 2-[p-(4-tetrahydropyranyl)-phenoxy]-butanoate.

11. An hypolipemic composition comprising an effective amount of at least one compound of claim 1 and an inert pharmaceutical carrier.

12. A composition of claim 11 wherein X is hydrogen or chlorine, $R_1$ is methyl and $R_2$ is methyl or hydrogen.

13. A method of lowering serum lipid levels in warm-blooded animals in need thereof comprising administering to said animals an hypolipemically effective amount of at least one compound of claim 1.

14. The method of claim 13 wherein X is hydrogen or chlorine.

15. The method of claim 14 wherein $R_1$ is methyl and $R_2$ is methyl or hydrogen.

16. The method of claim 13 wherein the compound is 2-methyl-2-[p-(4-tetrahydropyranyl)-phenoxy]-propanoic acid.

* * * * *